US006786904B2

(12) United States Patent
Döscher et al.

(10) Patent No.: US 6,786,904 B2
(45) Date of Patent: Sep. 7, 2004

(54) METHOD AND DEVICE TO TREAT VULNERABLE PLAQUE

(75) Inventors: Claas Döscher, Hamburg (DE); Wolfgang Daum, Groton, MA (US)

(73) Assignee: Triton BioSystems, Inc., Chelmsford, MA (US)

( * ) Notice: Subject to any disclaimer, the term of this patent is extended or adjusted under 35 U.S.C. 154(b) by 0 days.

(21) Appl. No.: 10/044,475

(22) Filed: Jan. 10, 2002

(65) Prior Publication Data

US 2003/0139739 A1 Jul. 24, 2003

(51) Int. Cl.$^7$ .................................................. A61B 18/18
(52) U.S. Cl. ......................... 606/28; 607/103; 623/902
(58) Field of Search ....................... 606/27, 28, 32–34, 606/41; 607/96, 98–101, 103; 600/13; 623/1.1, 1.11, 1.23, 902, 903

(56) References Cited

U.S. PATENT DOCUMENTS

| 4,448,198 A | | 5/1984 | Turner |
| 4,574,782 A | | 3/1986 | Borrelli et al. |
| 4,633,875 A | | 1/1987 | Turner |
| 4,790,311 A | | 12/1988 | Ruiz |
| 5,010,897 A | | 4/1991 | Leveen |
| 5,098,429 A | | 3/1992 | Sterzer |
| 5,160,828 A | | 11/1992 | Olsen |
| 5,685,847 A | * | 11/1997 | Barry ...................... 604/96.01 |
| 5,713,941 A | | 2/1998 | Robins et al. |
| 5,906,636 A | | 5/1999 | Casscells, III et al. |
| 6,238,421 B1 | * | 5/2001 | Gunther et al. ................ 607/13 |
| 6,264,595 B1 | * | 7/2001 | Delfino et al. .................. 600/1 |
| 6,451,044 B1 | * | 9/2002 | Naghavi et al. .............. 607/96 |
| 2002/0115931 A1 | * | 8/2002 | Strauss et al. .............. 600/420 |
| 2003/0139787 A1 | * | 7/2003 | Eggers et al. ................. 607/96 |

FOREIGN PATENT DOCUMENTS

| GB | 2 254 004 A | 9/1992 |
| WO | WO 94/12101 | 6/1994 |

OTHER PUBLICATIONS

Schmitz–Rode, T., Brune, M. Hoffmeister, K., Guenther, R.W. *High Frequency Induction Heating of Stents: An Approach to Control Intimal Hyperplasis and Tumor Ingrowth.* Supplement to J. of Radiology, vol. 197; Nov. 1995.

* cited by examiner

Primary Examiner—Michael Peffley
(74) Attorney, Agent, or Firm—Raymond A. Miller; Pepper Hamilton LLP; Lucy Elandjian

(57) ABSTRACT

A method and device to treat cardiovascular vulnerable plaque is provided by heating an implanted structure placed adjacent to a vulnerable plaque tissue to conduct heat into the vulnerable plaque tissue for a period of time. In a preferred embodiment, the implanted structure is a stent-like structure (SLS), and the heating of the implanted structure is a non-invasive inductive heating. The detecting of the vulnerable plaque tissue can be accomplished by techniques, such as Magnetic Resonance Imaging (MRI), infrared spectroscopy, thermography, blood tests, ultrasound, and X-ray, etc.

48 Claims, 15 Drawing Sheets

METHOD AND DEVICE TO TREAT VULNERABLE PLAQUE

FIELD OF THE INVENTION

The present invention generally relates to cardiovascular medicine. More particularly, the present invention relates to a cardiovascular heat delivery device and a method to treat a vulnerable plaque tissue.

BACKGROUND OF THE INVENTION

Coronary artery disease (CAD) is the most important cause of morbidity and mortality in today's society. Atherosclerosis (the most common form of arteriosclerosis, marked by cholesterol-lipid-calcium deposits in arterial linings), "hardening" of the arteries caused by plaques and plaque lesions, is the cause of myocardial infarction (MI). Some plaques are "hard and solid", and the others are "soft and squishy". It's the soft variety that is to worry about. Recently, this soft plaque has been called "vulnerable plaque" because of its tendency to burst or rupture.

Ischemic heart disease represents a continuum from stable angina to unstable angina to non-Q-wave MI to Q-wave MI. Patients whose angina becomes unstable are classified as having acute coronary syndrome (ACS). It was formerly believed that thrombosis leading to critical occlusion of coronary arteries at the site of atherosclerotic plaque rupture was the common cause of ischemic heart disease. It is now thought, that even plaque lesions that do not critically occlude coronary arteries can cause MI. ACS can be caused by the rupture of an unstable atherosclerotic plaque. Vulnerable plaques are usually those causing only mild to moderate stenosis and having a lipid-rich core and a thin, macrophage-dense, collagen-poor fibrous cap. Factors affecting plaque rupture include mechanical injury, circadian rhythm, inflammation, and infection. Progressive thrombosis and vasospasm may follow plaque rupture.

In the past, it was believed that atherosclerosis gradually and progressively led to the complete occlusion of an artery, thereby causing acute coronary events. However, it is now believed that rupture of a nonstenotic, yet vulnerable atherosclerotic plaque, frequently leads to an acute coronary syndrome.

It has been reported that rupture-prone (i.e., vulnerable plaques) typically have
 a thin fibrous cap,
 numerous inflammatory cells,
 a substantial lipid core, and
 (surprisingly) few smooth muscle cells.

It is believed that physical disruption of such a plaque allows circulating blood coagulation factors to meet with the highly thrombogenic material in the plaque's lipid core, thereby instigating the formation of a potentially occluding and fatal thrombus. Some believe these plaques cause <50% cross-sectional stenosis of the artery.

While the concept of plaque "vulnerability" implies the ability towards thrombosis, the term "vulnerable" was originally intended to provide a morphologic description consistent with plaques that are likely to rupture and can be seen as a specific cause of acute coronary syndromes. The phrase 'vulnerable plaque' was coined in the early 90's by Dr. James Muller of the University of Kentucky when he was working in Boston. Muller picked the word from his work against the arms race. Missiles in silos were vulnerable to Russian attack because they can be destroyed before they are used. Muller described that rupture-prone plaques are vulnerable, because something can come along and cause them to "misfire".

Mechanical stress and composition of plaques play an important role in plaque disruption. Mechanical forces can easily disrupt this plaque, even merely the vibration of the heart as it beats. The plaques are classified as either yellow or white using coronary angioscopy. Yellow plaques with an increased distensibility and a compensatory enlargement may be mechanically and structurally weak. As a result, mechanical "fatigue," caused by repetitive stretching, may lead to plaque disruption. Plaques with a high distensibility and a compensatory enlargement may be vulnerable.

The development of vulnerable plaques is not limited to the localized lesions but is a pan-coronary process. In patients with MI, all three major coronary arteries are widely diseased and have multiple yellow though nondisrupted plaques.

While a rupturing plaque can lead to a heart attack, most of the time nothing much bad happens. In fact, it appears that plaques break or rupture all the time, and those that trigger heart attacks are unlucky exception. It is believed that the large plaques visible on angiograms are often the healed-over and more stable remains of small vulnerable plaques.

One of the most important issues of vulnerable plaque is the fact that vulnerable plaques do not bulge inward. Instead, as plaque grows, it often protrudes outward, into the wall of the artery, rather than into the channel-lumen where blood flows. On an angiogram, everything can look normal. But when dissected after death, the arteries' walls are thick with plaque that could not yet be seen by angiogram.

Imaging the coronary arteries is a challenging task. The coronary arteries are difficult targets to track because of their small size, their tortuous course along the myocardium, and their complex cyclic excursions with cardiac and respiratory motions over distances much larger than their lumen size. Most limiting of all, motion, if not compensated, generates blurring and ghosting interferences not only from the coronary vessels themselves but also from the surrounding tissues. The key to succeed in imaging these highly mobile vessels is, thus, to freeze the motion. The development of ultrafast MRI has enabled steady progress to be made in coronary imaging by several groups in recent years. Among the various proposed methods the most successful are the segmented turbo-FLASH and spiral-scan gradient-echo techniques. Each produces a 2D image of the coronary arteries within a single breath-hold, acquiring 16–20 segments or spirals through k space in consecutive heart-beats. In order to freeze vessel motion each combines cardiac gating and breath holding and acquires the information exclusively during mid-diastole, the most quiescent period in the cardiac cycle.

By collecting a 2D image in less then 60 ms, EPI (Echo Planar Imaging) combined with a time-of-flight (TOF) EPI method offers a unique way to completely freeze the effect of both cardiac and respiratory motions.

At present, methods are being developed which allow a physician to view vulnerable plaque. Several invasive and non-invasive imaging techniques are available to assess atherosclerotic disease vessels. Most of these techniques are strong in identifying the morphological features of the disease, such as lumenal diameter and stenosis or wall thickness, and in some cases provide an assessment of the relative risk associated with the atherosclerotic disease. However, none of these techniques can yet fully characterize the composition of the atherosclerotic plaque in the vessel wall and, therefore, are incapable of conclusively identifying the vulnerable plaques.

High-resolution, multi-contrast, magnetic resonance (MR) can non-invasively image vulnerable plaques and characterize plaques in terms of lipid and fibrous content and identify the presence of thrombus or calcium. Application of MR imaging opens up whole new areas for diagnosis, prevention, and treatment of atherosclerosis.

Magnetic resonance imaging is proving to be a very useful non-invasive imaging technique in the study of the long-term evolution of atheroma lesions. Not only is it applicable for the diagnosis of atherosclerotic disease but also for the characterization of the cellular mechanisms implied in the development of vascular damage. The four main stages of lesions found in atherosclerosis, i.e. the onset of the lesion with the appearance of remodeling, the development of vulnerable plaque, thrombus formation, and the organization of the thrombus by connective tissue, have been reported, in both experimental animal models and in humans, from the images obtained by Magnetic Resonance Imaging (MRI). High-resolution, multi contrast MRI can non-invasively image vulnerable plaques and characterize plaques in terms of their different components (i.e., lipid, fibrous, calcium, or thrombus). This information may help physicians plan appropriate interventions. Other technologies may also help identify vulnerable plaques. These include: infrared spectroscopy, which may help provide a specific chemical signature for materials in a living structure, such as an artery wall; thermography, which may help find inflamed plaques with an associated higher temperature; and blood tests that may identify proteins resulting from inflammation of the arteries, a possible sign of "bad" plaque.

Once a vulnerable plaque is detected, the question arises as to how to treat it to reduce its tendency to rupture. Therefore, it is desired to find ways of making detected vulnerable plaques less likely to rupture in a way that can cause coronary occlusion, atherosclerosis or arteriosclerosis.

SUMMARY OF THE INVENTION

To treat vulnerable plaques that can be detected by imaging techniques, such as MRI, infrared spectroscopy, thermography, or blood test, the present invention provides a cardiovascular heat-target structure placed adjacent the detected or suspect intima wall of the inner vessel lumen and uses a targeted heating effect at the structure to treat the vulnerable plaque at that particular location. The heating procedure is believed effective to stabilize the vulnerable plaque and/or prevent the plaque from proliferation or from further development towards rupture.

The heating can be done in different ways. According to the present invention, a structure or target for the heating action is placed at the vulnerable plaque location and is used to direct heating to adjacent tissue. In one embodiment, the heating of the structure or target is accomplished non-invasively by induction from an external induction source, such as described in U.S. Pat. No. 6,238,421 or EP 1,036,574. In another embodiment, the heating of the structure or target is accomplished by placing an induction antenna energy source endoluminally inside of the heat-target structure. Other embodiments for heating the structure or target can include direct resistive heating via invasive endoluminal electrical cables; non-invasive focused ultrasound; endoluminal invasive ultrasound transducer placed inside the structure; invasive endoluminal microwave probe; optical, preferable infrared or lasers, heating from an endoluminal source within the structure; or optical energy supplied in coordination with replacing the blood for a short interval by an optically transparent media, such as carbon dioxide gas, water or saline. In a preferred embodiment described below, the heating of the structure is achieved by non-invasive inductive heating.

DETAILED DESCRIPTION OF THE PREFERRED EMBODIMENT

1. Overview of Method

The present invention provides methods of and apparatuses for treating cardiovascular, vulnerable plaque tissue by heating an implanted structure placed adjacent the vulnerable plaque tissue to conduct heat into the vulnerable plaque tissue for a period of time. In a preferred embodiment, the implanted structure is a stent-like structure (SLS), and the heating of the implanted structure is a non-invasive inductive heating. The detecting of the vulnerable plaque can be accomplished by a variety of techniques, such as Magnetic Resonance Imaging (MRI), infrared spectroscopy, thermography, blood tests, ultrasound, and X-ray, etc. In the following embodiments, the use of a SLS and MRI is described as an example for detecting and treating vulnerable plaque.

Figure 1:
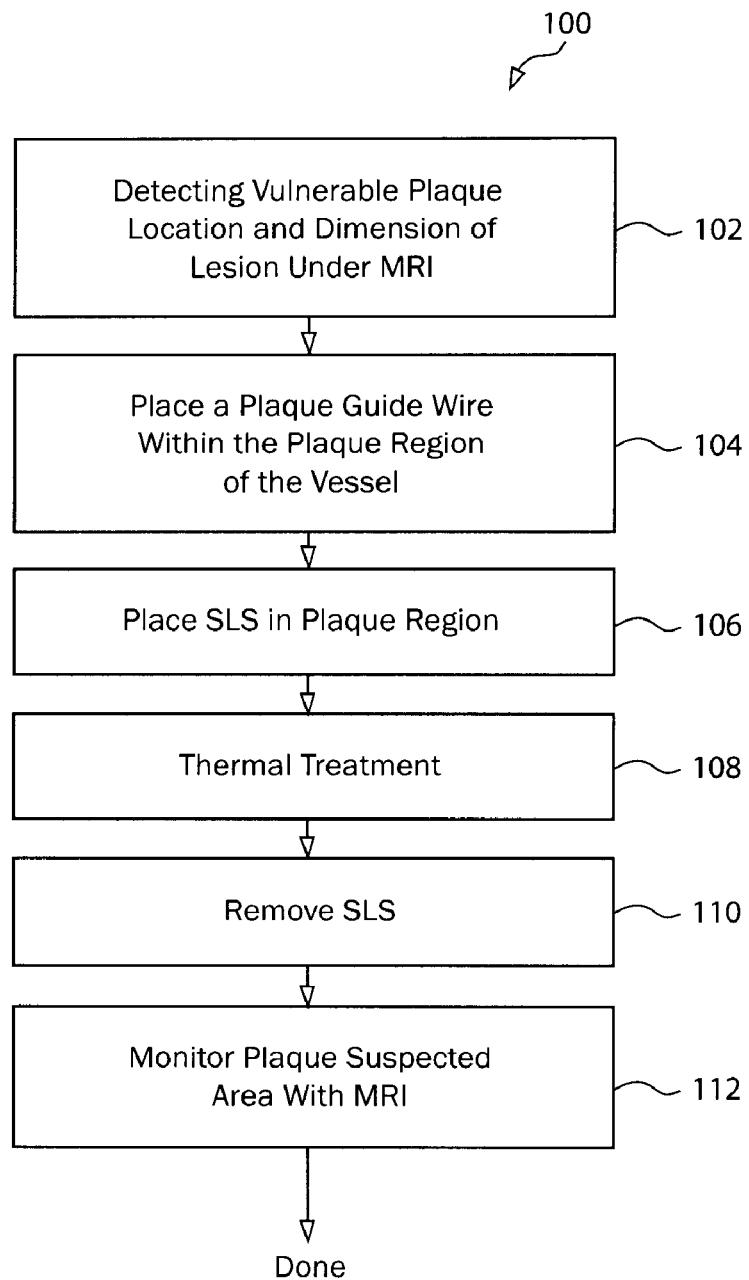
FIG. 1 illustrates a flow chart of a process of treating vulnerable plaque by one-time thermal treatment of a heat-target structure in accordance with the principles of the present invention.

FIG. 1 illustrates a flow chart of a process 100 of treating vulnerable plaque by one time thermal treatment of a heat-target structure. The process 100 starts with a step 102 of detecting the vulnerable plaque's location and measuring the dimension of the vulnerable plaque lesion. A guide wire may be placed by conventional means to assist in the placement of the SLS in a step 104. Then, the SLS is placed in a vulnerable plaque region in a step 106. Then, the SLS is thermally treated in a step 108, for example, heated non-invasively by induction from an external induction source, such as described in U.S. Pat. No. 6,238,421 or EP 1,036,574; by placing an induction antenna energy source endoluminally inside of the heat-target structure; direct resistive heating via invasive endoluminal electrical cables; non-invasive focused ultrasound; endoluminal invasive ultrasound transducer placed inside the structure; invasive endoluminal microwave probe; and optical, preferable infrared or lasers, heating from an endoluminal sourced within the structure. To aid the latter, it may be desired to replace the blood for a short interval by an optically transparent media, such as carbon dioxide gas, water or saline.

Next, where the SLS is temporary, the SLS is removed in a step of 110. The vulnerable plaque region is monitored by MRI in a step 112. If indicated, the whole procedure as described in FIG. 1 can be repeated several times over days, weeks or months.

Figure 2:
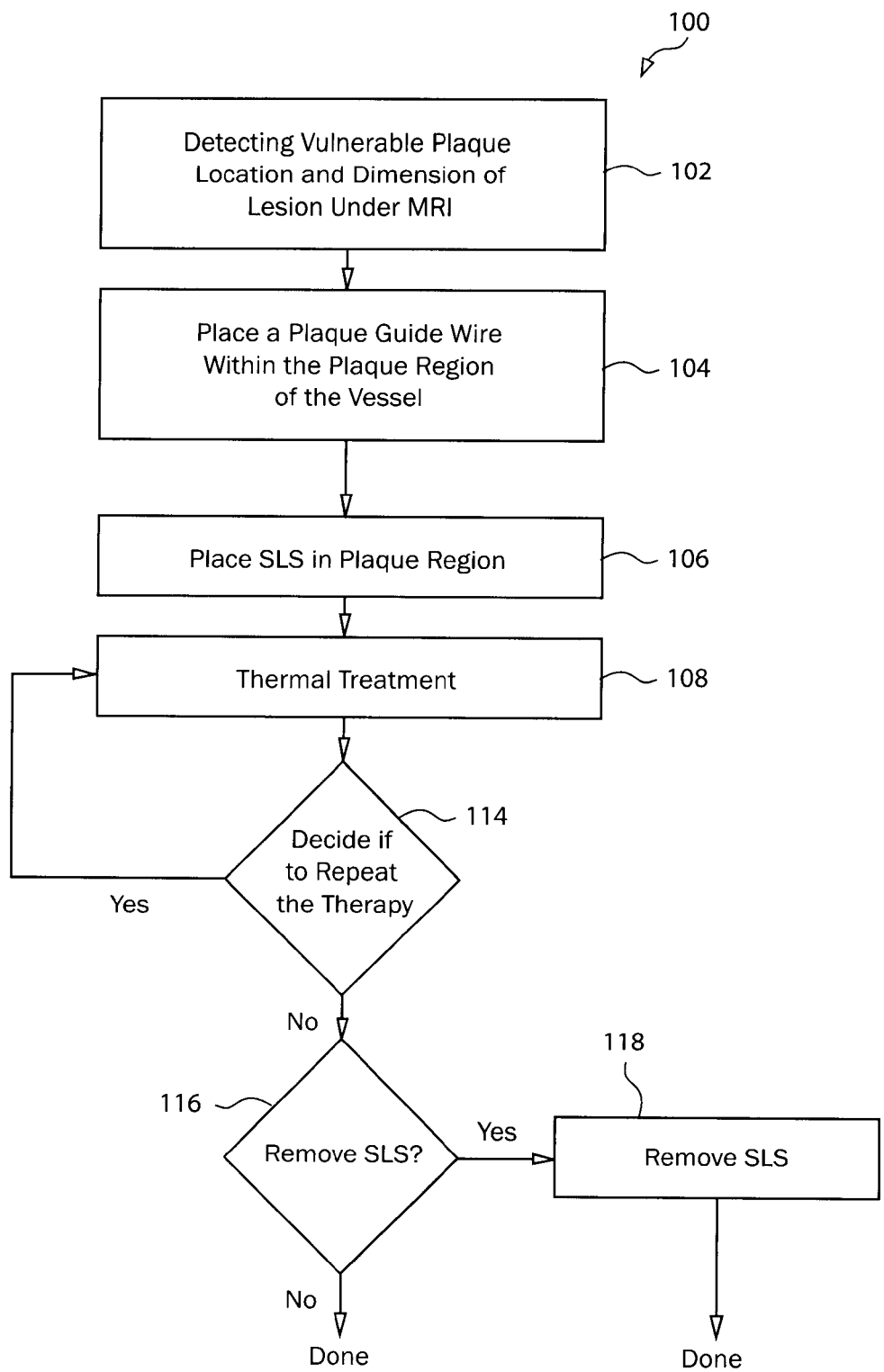
FIG. 2 illustrates a flow chart of a process of treating vulnerable plaque as shown in FIG. 1 and removal of the heat-target structure in accordance with the principles of the present invention.

The procedure as described in FIG. 1 can be repeated in a defined routine as shown in FIG. 2. Such a routine can last over days, weeks or months. One may decide to heat the SLS once a week for some seconds or minutes in a treatment process, lasting some weeks in a step 114. After such a routine, the SLS may be left in the vessel in a step 116, or if technical and anatomically practicable, be removed in a step 118.

2. Identifying the Area to be Treated and Placing the SLS

Figure 3:
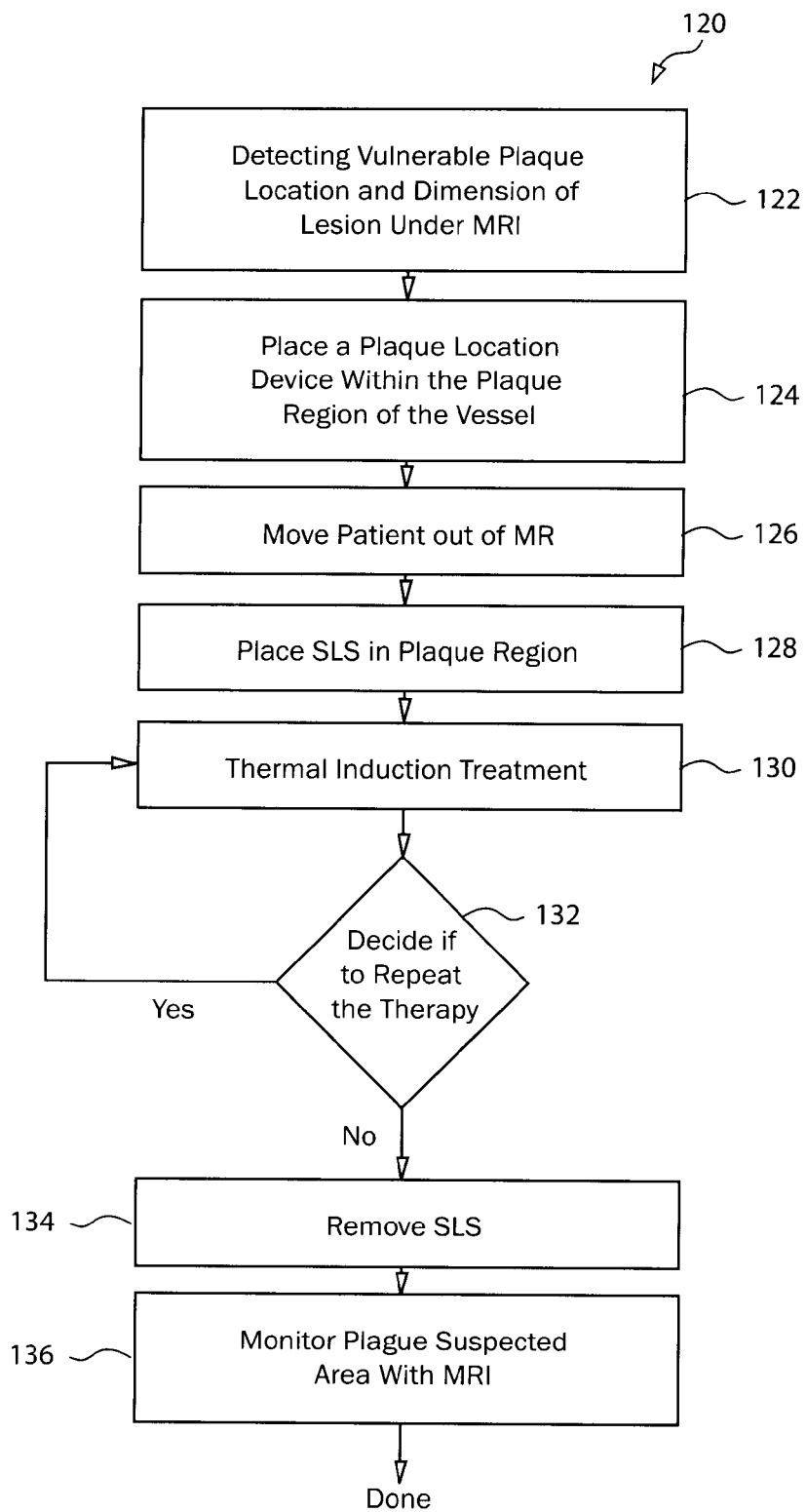
FIG. 3 illustrates a flow chart of a process of treating vulnerable plaque by one time inductive thermal treatment of the heat-target structure in accordance with the principles of the present invention.

In a preferred embodiment, non-invasive inductive heating by an external antenna is used for heating the SLS. The SLS is preferably made out of a material with high magnetic susceptibility (see details below). FIG. 3 illustrates a flow chart of a process 120 of treating vulnerable plaque in a patient's cardiovascular vessel. The process 120 starts with a step of detecting a vulnerable plaque's location in a patient and measuring the dimension of the vulnerable plaque lesion under the MRI in a step 122. A plaque location device is placed in the plaque region of the vessel in a step 124. Then, the patient is moved out of the MRI in a step of 126. Next, the SLS is placed in the plaque region in a step 128. Then, a thermal induction treatment is performed in a step 130. Then, the process 120 determines whether the treatment should be repeated in a step 132. If yes, the process 120 returns to the step 130. If no, the SLS may be removed in a step 134. The vulnerable plaque region is monitored with the MRI in a step 136. This treatment can be repeated as many times as desired. For monitoring the result of the inductive heating treatment, the SLS may be removed due to the effect of MRI on its material.

To place an SLS in a patient's vessel, a guide wire or guiding tube is placed in the vessel first. FIGS. 4a–4d illustrate this process in detail for a suspected vulnerable plaque lesion in any type of coronary, for example, the left coronary artery as shown. In FIGS. 4a–4d, a general anatomical overview is illustrated (dimensions shown are not anatomical). A guide wire or guiding tube 9 is pushed cranialis (in upper direction) through a descending aorta 3, passing a left subclavia 5, left common carotid artery 6, and the brachiocephalic trunk 7 down into an ascending aorta 8. A tip 10 of the guide wire or guiding tube 9 ends just before the left ventricle facing the vessel 1.

Figure 4A:
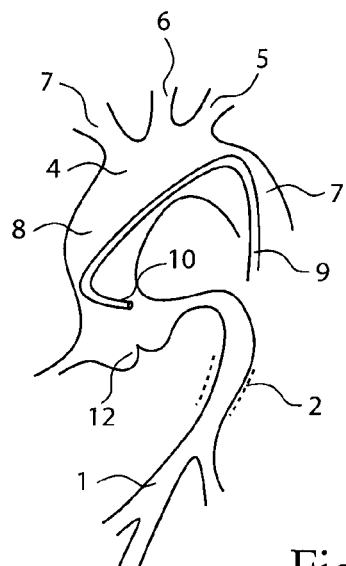
FIGS. 4a–4d illustrate one embodiment of a localization device to locate suspected vulnerable plaque regions under an imaging device, such as MRI, in accordance with the principles of the present invention.
Figure 4B:
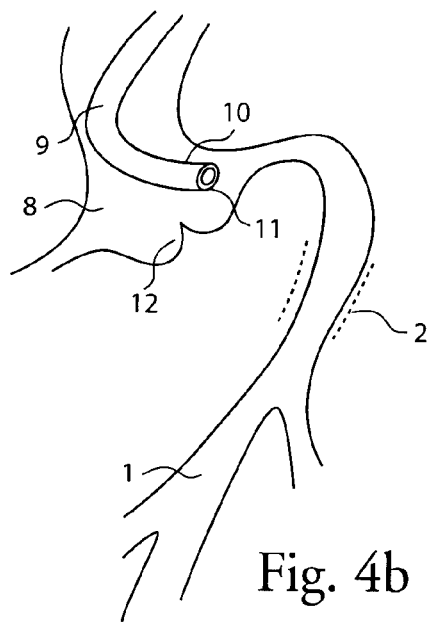

FIG. 4b shows the region of interest in a higher enlargement. To place a guide wire in a non-MR environment is state of the art. An MR compatible guide wire is typically non-magnetic and non-metallic. In a high alternating field, electrical currents are induced that would heat up the metallic wire and would easily burn the patients vessel and blood cells and could cause serious injuries.

Figure 4C:
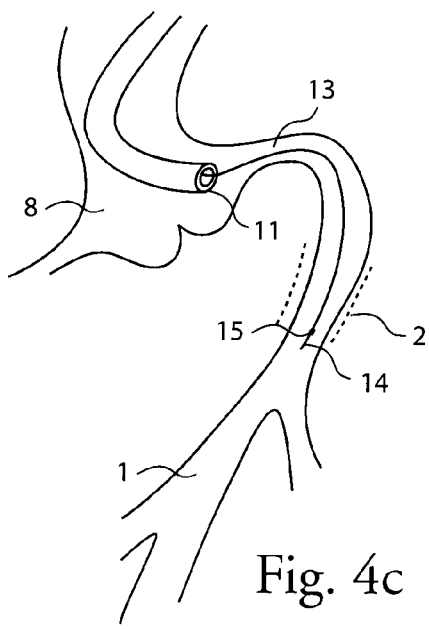

In a preferred embodiment, the guide wire or guiding tube 9 is made out of an elastic non-magnetic material, preferable a plastic like material, such as Polyethylene (PE), Polypropylene (PP), Polyurethane (PU), or Polymethyl Methacrylate (PMMA), that can be pre-bent at its distal end in a shape, such as a J shape, for coronary applications. FIGS. 4b–4c show an opening 11 of an inner lumen of the guide wire 9, out of which a guiding non-magnetic and non metallic localization wire 13 is pushed. This localization wire 13 is also preferably made of plastic or encapsulated glass fiber and has at its tip 14 an MR visible marking 15.

Figure 4D:
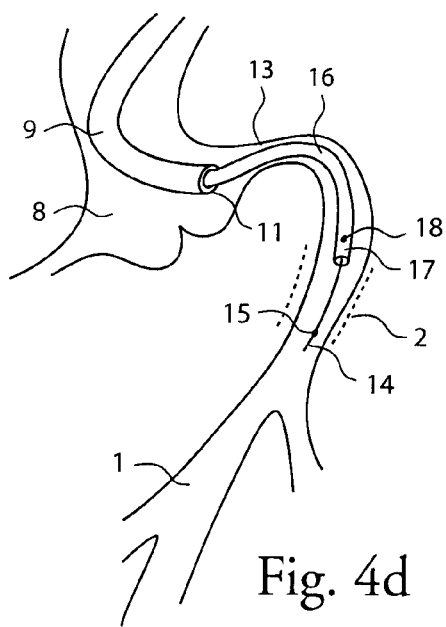

In one embodiment of the invention, the localization wire 13 is made out of metal, but electrical decoupled by at least one electrical LC resonant circuit at its proximal end. This MR visible marking 15 is made of a material that gives an active MR signal (positive artifact), such as Gadolinium or other rare earth metals, or a passive MR signal (negative artifact), such as titanium, stainless steel, platinum or gold, just to name a few. The localization wire 13 is placed in such a way in the vessel 1, that the marking 15 locates the distal end of the subject vulnerable plaque region 2 as shown in FIG. 4c. Finally, a marking tube 16, which fits around the localization wire 13 and in the lumen of the guide wire or guiding tube 9, is pushed out of the guide wire or guiding tube 9 into the vessel 1 as shown in FIG. 4d. This marking tube 16 is also made of a non-metallic and non-magnetic material. The marking tube 16 has a MRI visible marking 18 at its tip 17.

The principle of the marking 18 is the same as the marking 15 of the localization wire 13, except that the marking 15 can be ring moulded in the material of the marking tube 16 or mounted on top or inside of it. The marking tube 16 is placed in such a way in the vessel 1 that the marking 15 locates the other end (proximal end) of the subject vulnerable plaque region 2. Both markings 15 and 18 are identified under an MRI image. The subject vulnerable plaque region is detected, and the dimension of the vulnerable plaque can be measured between the marking 15 and the marking 18.

Figure 5:
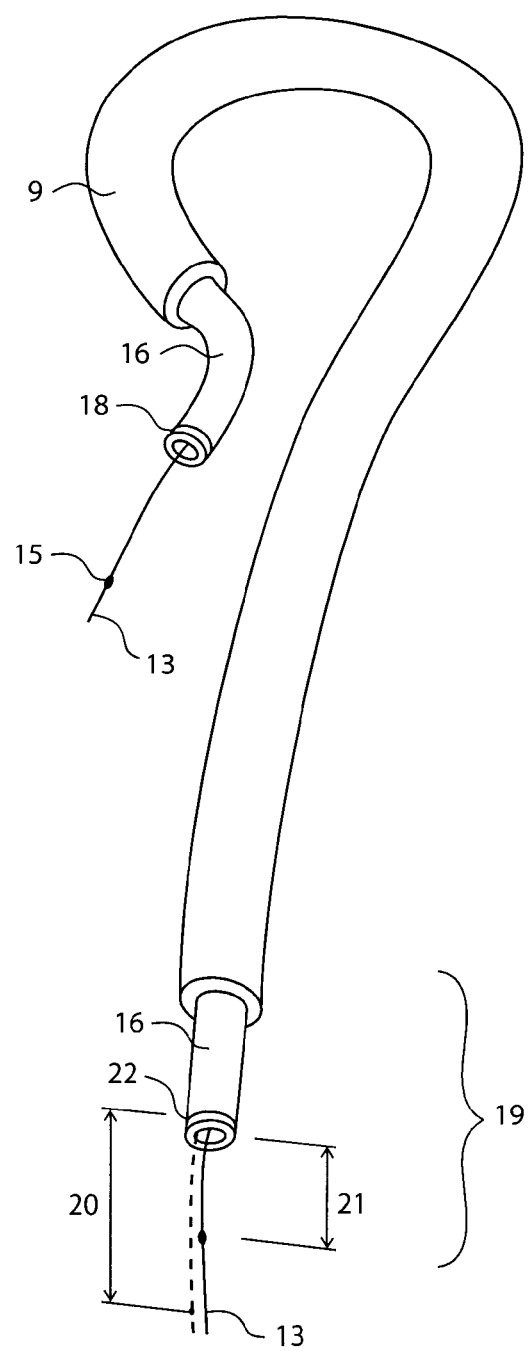
FIG. 5 illustrates one embodiment of a localization wire-tubing system without anatomy, in accordance with the principles of the present invention.

As seen in FIG. 5, at the proximal end 19 of the guide wire or guiding tube 9, the length of the subject vulnerable plaque region 2 can be calculated by subtracting the end-position/end-distance 20 of a given point on the wire 13 relatively to a given point 22 on the marking tube 16 from the initial starting-position/starting-distance 21 of a given point on the wire 13 relatively to the given point on the marking tube 16. Once the length of the subject vulnerable region is determined, one can then select a length of the corresponding SLS to be placed in the vulnerable plaque region 2 as shown in FIGS. 4a–4d.

Figure 6A:
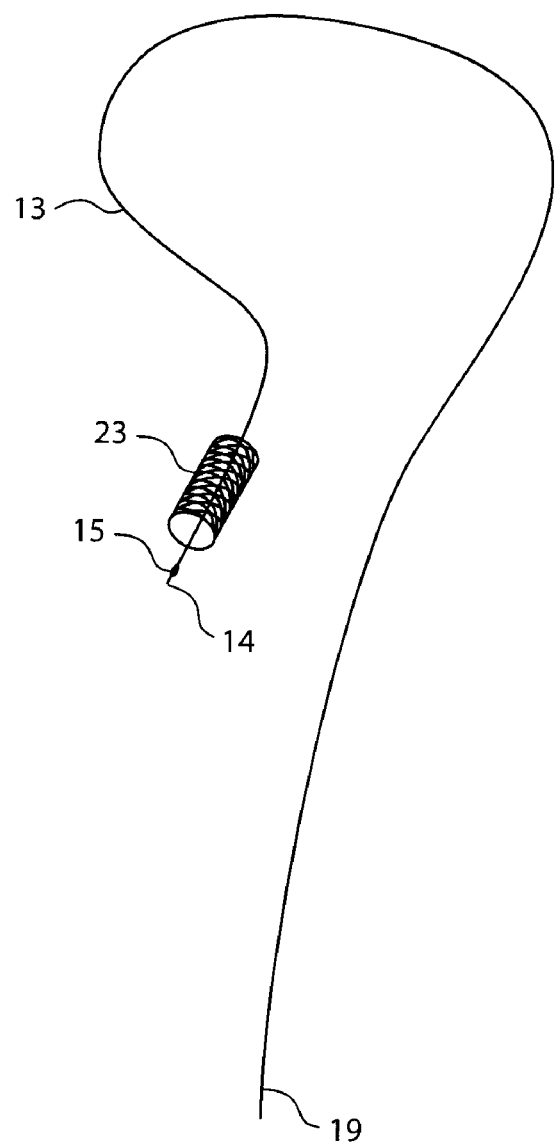
FIG. 6a illustrates one embodiment of a heat-target structure, such as a stent-like structure (SLS), on wire, in accordance with the principles of the present invention.

The guide wire or guiding tubing 9 and the marking tubing 16 are removed by pulling them back towards the proximal end 19. After having moved the patient out of the MRI, the SLS 23 is placed by mechanical pushing means into the vulnerable plaque region on top of the localization wire 13 as shown in FIG. 6a. This procedure can be performed by using balloon catheter mechanism, which is state of the art and is therefore not further described here.

3. Design of the SLS or Heating Target

Because the SLS or heating target will be placed within a blood vessel in such the same manner as a conventional stent, that stents may be a useful starting point for SLS design.

Today's conventional stents are visible under MRI. Stents made of stainless steel show a rather large image distortion or a blur of the image, referred to as image artifact. This image artifact is created by a local distortion of the MR magnetic field conditions due to the magnetic susceptibility of the stent material used. Titanium-Nickel and even better pure Titanium stents offer a much lower or better controllable artifact, especially when used with optimized MRI sequences. On the other hand, these materials comprise a low magnetic susceptibility and, hence, are harder to heat up by induction.

However, there are several new factors a designer of a SLS has to consider, since the SLS differs in some ways from a state of the art stent:

SLS is preferably made of a material that allows easy inductive heat up and preferably has a high magnetic susceptibility.

The primary purposes of using a SLS are to be heated and to deliver heat to adjacent vulnerable plaque tissue. By contrast, a stent must hold a blood vessel open and must provide a high radial force. A SLS does not have to provide this radial force. It can and may be constructed of lighter and more flexible materials.

Because a SLS is not intended to be a permanent implant, there is preferably a mechanism to reposition and remove the SAS. It might be necessary to relocate the SAS many times in the same patient to different vulnerable plaque regions or along a very long vulnerable plaque region. The above described procedure is then repeated many times.

Because a SLS may address heat delivery to vulnerable plaque tissue that may not be uniformly cylindrical, the stent need not necessarily be cylindrical in form and need not be uniform. It could have one region that has greater or lesser structure or mass to provide differential heating to different parts of the adjacent tissue. For example, one half of the cylinder might have a denser lattice structure or a thicker wall to absorb more heating energy or deliver more heating effect.

As more is learned about the exact biochemistry of stabilizing and/or inhibiting growth of vulnerable plaque tissues, the SLS may be augmented with drugs that are releasable on activation at the temperature achieved by heating, where such drugs can cause or aid the stabilizing or growth-inhibiting effects.

Since the SLS does not have to have a strong radial (to hold vessel open) force, it can be made out of a thinner tube than a typical stent. This might have the effect that the image artifact resulting from the SLS is not too large or in an allowable range. This would have the benefit to place the SLS under an MRI. A further advantage is that the MR itself may heat up the SLS with a different gradient coil switching frequency.

It is appreciated to a person skilled in the art that a SLS can be a permanent implant as a stent is. For example, it may be valuable to leave the SLS as an implant in the vessel to repeat thermal therapy after periods of time. Hence, in one embodiment of the present invention, a SLS is made as a permanent implant.

Figure 6B:
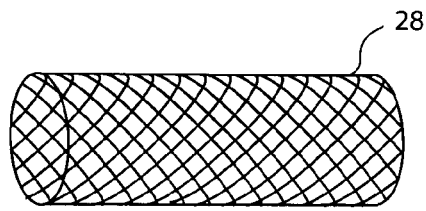
FIGS. 6b–6g illustrate a variety of different embodiments of the heat-target structure in accordance with the principles of the present invention.
Figure 6C:
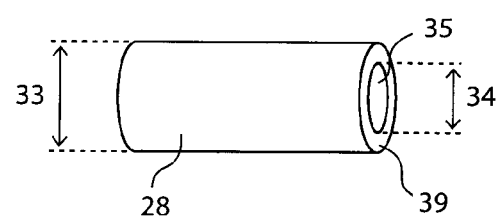
Figure 6D:
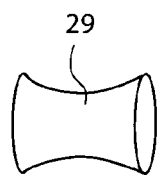
Figure 6E:
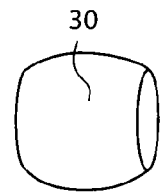
Figure 6F:
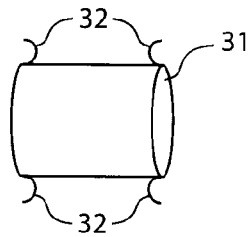
Figure 6G:
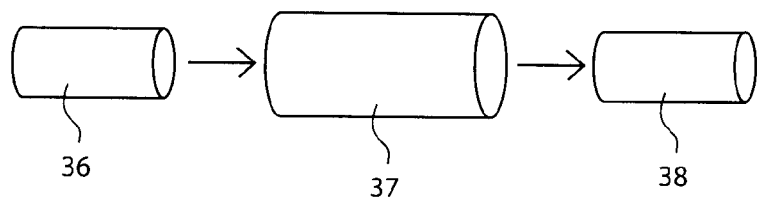

FIGS. 6b–6g illustrate different forms of SLS. As shown in FIGS. 6b–6c, a SLS has a tubular body 28. The tubular body 28 is cut out of a tube with an outer diameter 33 and an inner diameter 34 that defines a lumen 35. The tube wall 39 is cut into a mash alike structure, not shown in the figure, similar to a stent. The preferred cutting method for this lattice, or netting, or mash alike structure is laser cutting. The SLS can also be made as a woven wire mash or wire netting. The SLS is held in place by expanding it to the vessel wall and holding it with the marking wire 13. It might also be preferable to give it more stabilization by giving it a concave 29 (FIG. 6d) or convex 30 (FIG. 6e) form in order that the SLS is pushing parts of it into the vessel wall and clamping for fixation. In FIG. 6f, a SLS 31 may also include little hooks 32 again clamping itself into the vessel wall. Also, in FIG. 6g, a SLS can be expanded from its starting diameter 36 to its working diameter 37 back to its removing diameter 38. Starting diameter 36 and ending diameter 28 do not have to be the same.

4. Induction Heating of the SLS

Figure 7:
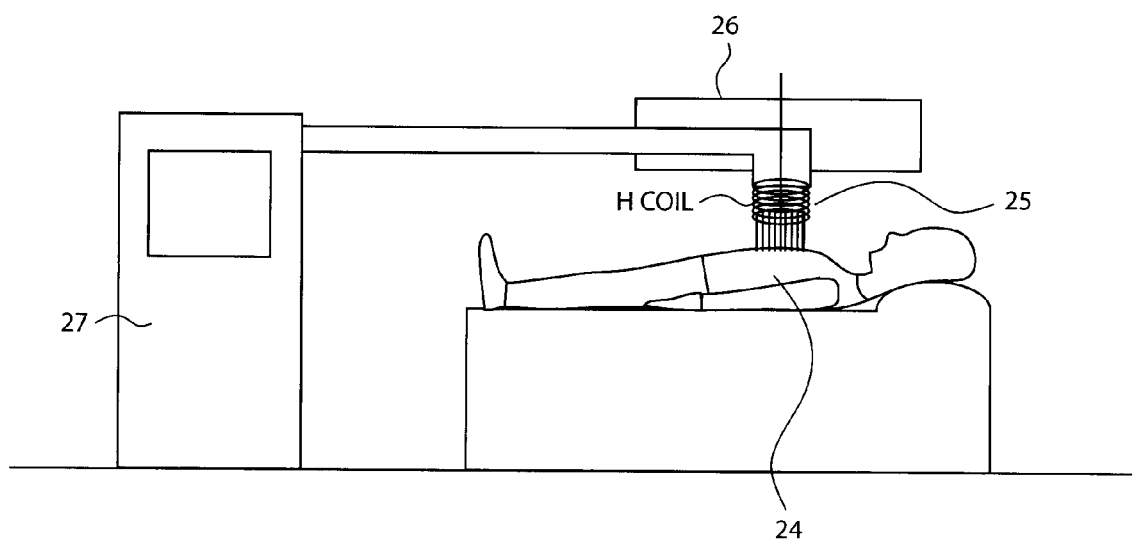
FIG. 7 illustrates one embodiment of an induction heating system in accordance with the principles of the present invention.
Figure 8:
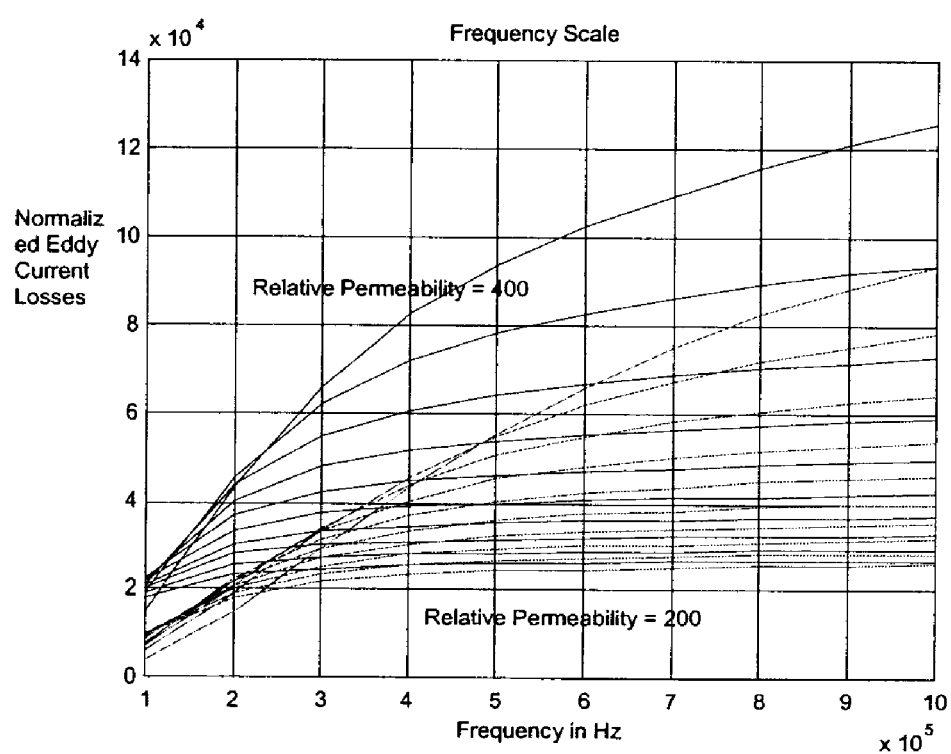
FIG. 8 illustrates a schematic view of Eddy Current vs. frequency with permeability as a parameter in accordance with the principles of the present invention.

The induction heating process is carried out with a heating device as illustrated in FIG. 7. The patient is laying underneath the sending antenna H coil (H=magnetic field). The power is generated by a generator and amplifier unit 27, and electrical current flows to a resonant circuit 26 which has to be close to the energy sending antenna H coil to avoid parasite inductances. The desired frequency range is preferably between 50 Hz and 2 MHz, and more preferable between 100 kHz and 900 kHz.

During the inductive heating process, electric energy is transmitted to the SLS by the H-field, which by the means of an induction coil flowing alternating current produces a magnetic alternating field, which consequently has a certain current in the SLS. The electric energy supplied by the induction coil is first converted in magnetic energy, which is then converted in heat in the SLS. The current density in material piece is determined through the so-called skin-effect. The highest current density is reached at the SLS surface. The current density drops off inside exponentially. No current flows within the material anymore.

The inductive heating power (P) is:

$$P = k \cdot I_{IND}^2 \cdot \sqrt{\mu \cdot \rho \cdot f}$$

wherein:
k=Constant
$I_{IND}$=Current in the induction coil
$\mu$=Relative permeability of material piece and $\mu_0$
$\rho$=Specific resistance of material piece in $\Omega$ mm$^2$/m
f=Frequency in Hz
(magnetic susceptibility+1=relative permeability)

The constant k can be empirically determined. It contains the coupling factors of the physical arrangement. But as the formula shows, one can discern proportions. The current in the transmitting coil $I_{IND}$ is quadratic, the specific resistance $\rho$, the permeability $\mu$ and the frequency f are in the root of the power. Resistance and permeability are set in advance by material. The primary goal is to increase frequency and induction current. Increasing the frequency simultaneously increases absorption and decreases the skin-effect.

The penetration depth of the current in the wire of the SLS, due to the skin-effect, is:

$$\delta[m] = \sqrt{\frac{\rho}{\pi \cdot \mu \cdot f}}$$

The equation is valid wherein the material piece diameter is at least twice as big as penetration depth of the current. If one increases the specific resistance, the penetration depth of the medium increases as well. With a given material, the skin-effect requires a certain minimal frequency at which the coupling eddy currents are effective. When keeping frequency lower, the heating effect is worse. When increasing frequencies, the heating effect is better.

The correlation among the specific resistance, permeability and coupling power is important. If the specific resistance of the material decreases, one can take advantage of the skin-effect even at low frequencies.

The basic principle of excitation of the heating process is based on a L-C-parallel-resonant-circuit 26. Provided that the wall thickness of the SLS is very small compared to the diameter D of the sending antenna conductor loop (d/D<0.001, d is the diameter of a wire), it is possible to use a simple solution for inductivity L:

$$L = n^2 \cdot \mu_0 \cdot R \cdot \ln\left(\frac{2R}{d}\right)$$

R is radius of conductor loop, d diameter of a wire.

As a result, the resonance frequency of the resonant circuit 26 is $$\omega = \frac{1}{\sqrt{LC}}$$

The blind current through the coil is calculated as follows:

$$I = U \cdot \omega \cdot C$$

This current causes magnetic field with field strength H.

The SLS should not be positioned within the conductor loop. Otherwise, the coil must be placed around the body, but the inductivity of the coil increases with the radius. It would be an advantage if one places the SLS at 5 cm to 15 cm outside the coil. If one varies the radius R of the transmitting aerial keeping the distance x to transmitting aerial constant and the simplified assumption of a constant coil's current I in the transmitting aerial, a maximum field strength H in case R≈x is obtained.

As long as x<λ/2π, a round coil (conductor loop) is valid for H along coil's axle:

$$H = \frac{I \cdot N \cdot R^2}{2\sqrt{(R^2 + x^2)^3}}$$

wherein:
N: Number of windings
R: Circuit radius
x: Distance to coil's middle in x-direction
λ: Wave length This accounts for the coil's middle point, where:

$$H = \frac{I \cdot N}{2R}$$

It may be necessary to develop a type of SLS that retains all the therapeutic and technical features and improves the ratio between the supply of electromagnetic energy and the transformed heat from the SLS. There is still the task of increasing the efficiency rate of an appropriate type of appliance for warming the new SLS. An objective of the present invention is to self-regulate temperature by means of material modification and application of the Curie effect.

5. Materials Selection for the SLS

The particular advantage of a new SLS is mainly to be found in the use of a material that possesses increased receptivity for the electromagnetic field strength, which requires a high degree of magnetic permeability. A further phenomenon is also put to use, in which the warming of the SLS occurs by means of the incidental eddy current losses. Thus, the eddy current is increased through the correct choice of the material and the construction of the SLS to the degree that considerably more heat is absorbed with very little additional technological effort.

When one increases the frequency of the induced H-field above, a characteristic and material specific value $f_w$, the eddy currents then dominate the other effects.

$$f_w = 8 \cdot p / \mu \cdot D^2$$

wherein:
p: the specific of the resistance material;
μ: the product of permeability and of relative permeability; and
D: the thickness of the material.

At high permeability, frequency typically is far below that of commonly used generator frequencies.

The aforementioned leads to reduced demand for electrical power and thus a reduction in technical complexity for a power supply system. To this end, it is especially advantageous if the metal alloy has a permeability of more than 100. Permeability preferably amounts to several thousand. The preferred metal alloy is a nickel-iron alloy, but other alloys, such as nickel-copper, nickel-palladium, palladium-cobalt and nickel-silicon, etc., may be utilized.

A further decisive advantage is that the metal alloy possesses a Curie temperature that assures that a SLS is maintained at a temperature at which tissue proliferation is stopped. The Curie point of the material with the help of the alloy composition can, for example, be designed to allow temperatures ranging between 40° C. and 60° C., preferably between 42° C. and 45° C. When the Curie temperature has been reached, further temperature increase does not occur. The Curie temperature, therefore, is the maximum temperature limit and prevents the stent from overheating. This eliminates the need for a temperature monitoring device, and a SLS warming device can be achieved in a simple and cost effective manner.

It is also an advantage when the SLS is coated with a highly electro-conductive material as this results in improved heat distribution. The coating has the further advantage of being corrosion resistant. It is also sensible to coat the inner side of the cylindrical mesh-like SLS device, which faces the vessel lumen with a poor heat conductor so that the warmth created in the SLS by induction flows to the outer side of the SLS and helps treat the vulnerable plaque tissue.

The device for warming a SLS in a living being distinguishes itself especially through an optimally designed induction coil delivery system, which has, on the one hand, a small diameter, and on the other hand, a relatively large length for emitting the magnetic field.

Especially effective is an induction coil with preferably one to five coil windings and a diameter of 30 cm.

A SLS may include a cylindrical body made of a wire structure which is laser cut from a small tube. The cylindrical body has an expanded diameter of 1–10 mm (1 to 3 mm for cardio-vessel SLS, 4 to 8 mm for peripheral vascular SLS, 2 to 10 mm for aortic SLS), depending on the extent of the vessel vulnerable plaque of 4 to 100 mm length. Wall thickness of a SLS is in the range of 0.3 to 1.0 mm.

The material for a SLS that can be effectively warmed by induction is preferably, for example, an alloy of nickel and iron. The ratio of nickel to iron is chosen so that the relative permeability of the nickel-iron alloy has an approximate value of 100,000, and the Curie temperature is at approximate 50° C. to 55° C. With that relative permeability value, the alloy is designed to absorb the optimal amount of magnetic field energy above which spontaneous magnetization disappears. It separates the disordered paramagnetic phase at T>Tc from the ordered ferromagnetic phase at T<Tc, where Tc is Curie Temperature). It is appreciated that a SLS in accordance with the present invention is made of a material that has a relative magnetic permeability of higher than the state of the art stents, for example, higher than 2,000, and most likely at 100,000 or more.

A SLS made of this alloy can be coated with gold or with a different overlay so that the entire arrangement becomes corrosion resistant and highly conductive. Gold is not the material of choice in stents because it seems to extent the instent-restenosis effect. However, since a SLS can be removed from the vessel, gold coating can be used here.

Figure 9:
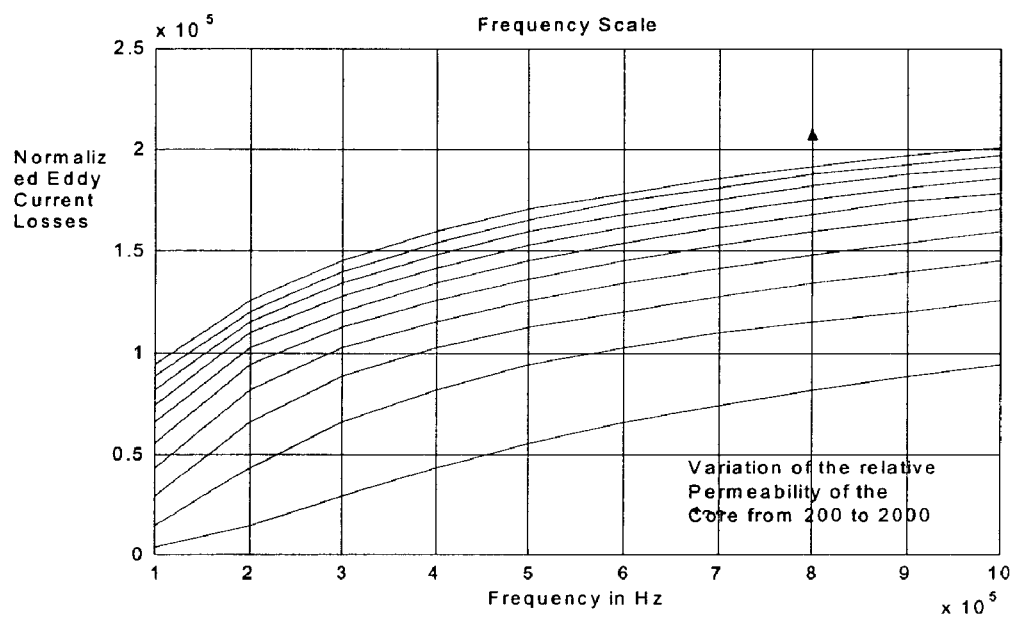
FIG. 9 illustrates a schematic view of Eddy Current vs. frequency with permeability as a parameter in accordance with the principles of the present invention.

When simulating a SLS with a core and heat conductive gold coating as illustrated in FIGS. 8 to 14, the following assumptions are made. The gold coating is varied up to a thickness of 5 $\mu$m with 0.5 $\mu$m increments. The frequency ranges from 100 kHz to 1 MHz. Relative magnetic permeability is 1 to 2,000. The investigated parameter of all simulations is the in-coupled heat generated or lost due to eddy currents. FIG. 9 shows the eddy current losses vs. frequency of the excitation, with the coating thickness being 0.5 micrometers.

Figure 10:
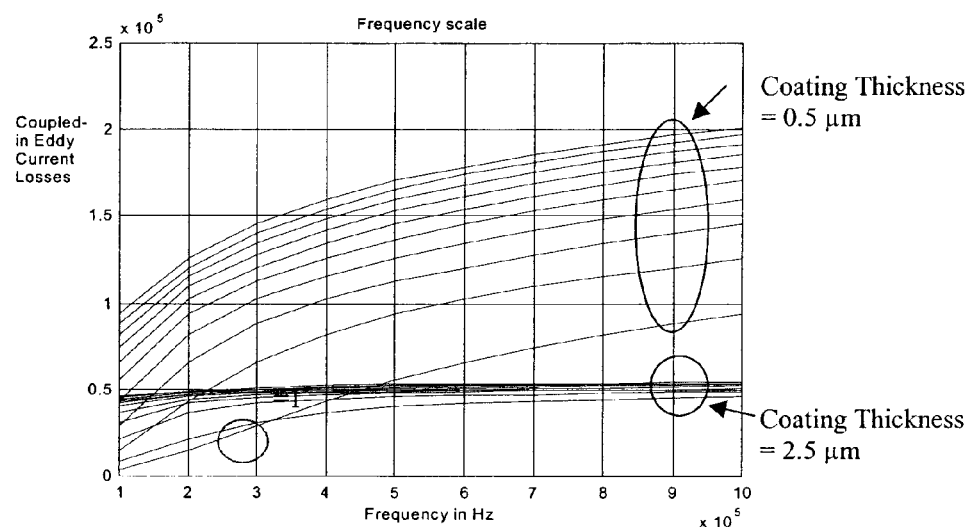
FIG. 10 illustrates a schematic view of Eddy Current vs. frequency with coating thickness as a parameter in accordance with the principles of the present invention.
Figure 11:
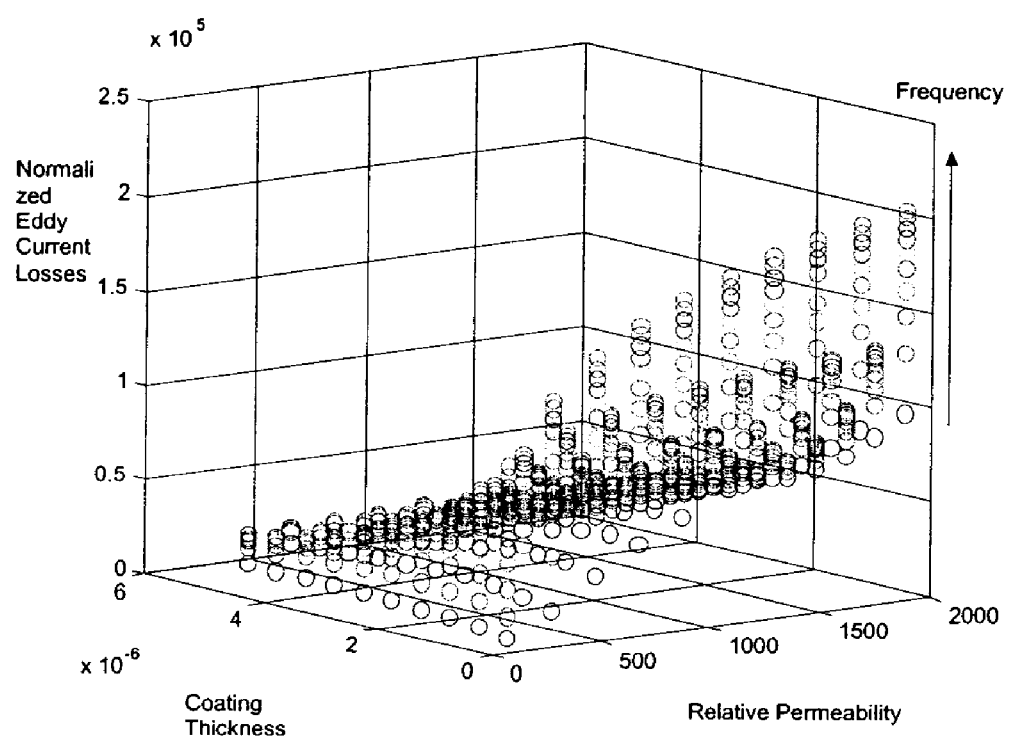
FIG. 11 illustrates a schematic view of Eddy Current vs. frequency and permeability in accordance with the principles of the present invention.
Figure 12:
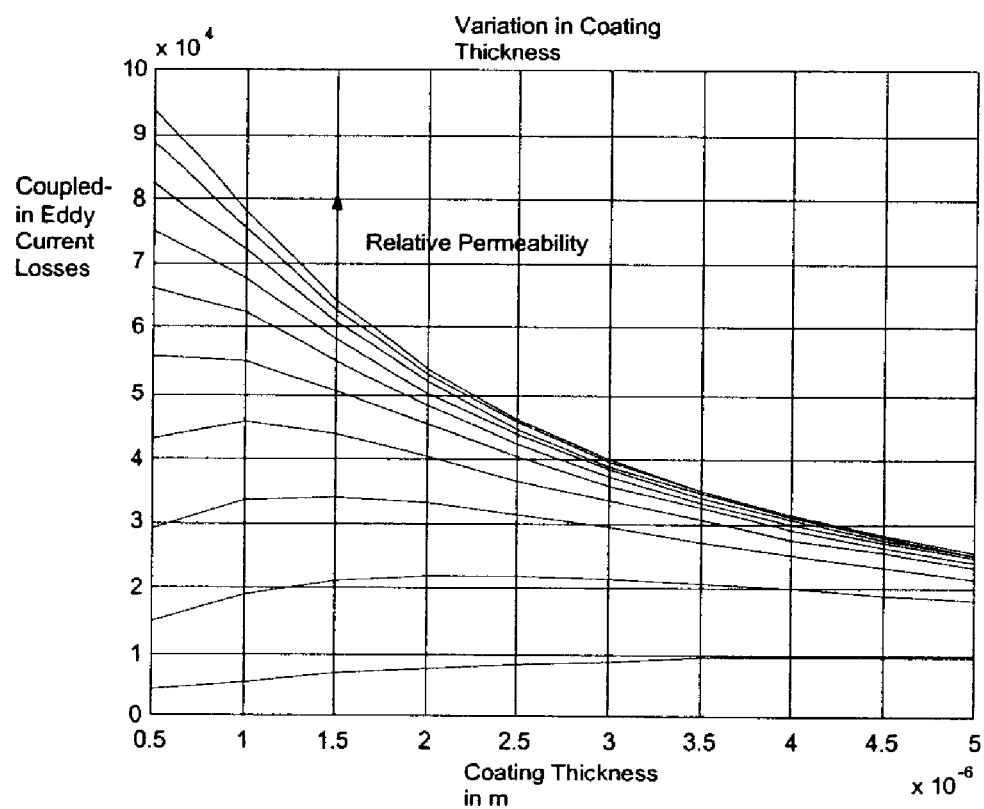
FIG. 12 illustrates a schematic view of Eddy Current vs. coating thickness with permeability as a parameter in accordance with the principles of the present invention.

FIG. 10 shows two series of curves for increasing permeability with one having a coating thickness of 0.5 $\mu$m and the other 2.5 $\mu$m. FIG. 11 shows the in-coupled power relative to the thickness of the coating, the permeability and the frequency. It can be seen that the maximum value is achieved with the thinnest coating (0.5 $\mu$m) and highest permeability (2,000) as well as the highest frequency (1 MHz). Minimum and maximum permeability differ by a factor of 45 compared to uncoated pure steel by 200,000. In FIG. 11, the coating thickness is varied with fixed frequency and permeability. FIG. 12 shows variation in the coating thickness. The maximum in-coupled eddy current losses is also a function of the relative permeability. Above a value of 1,000, the coating thickness lies under 0.5 $\mu$m.

Figure 13:
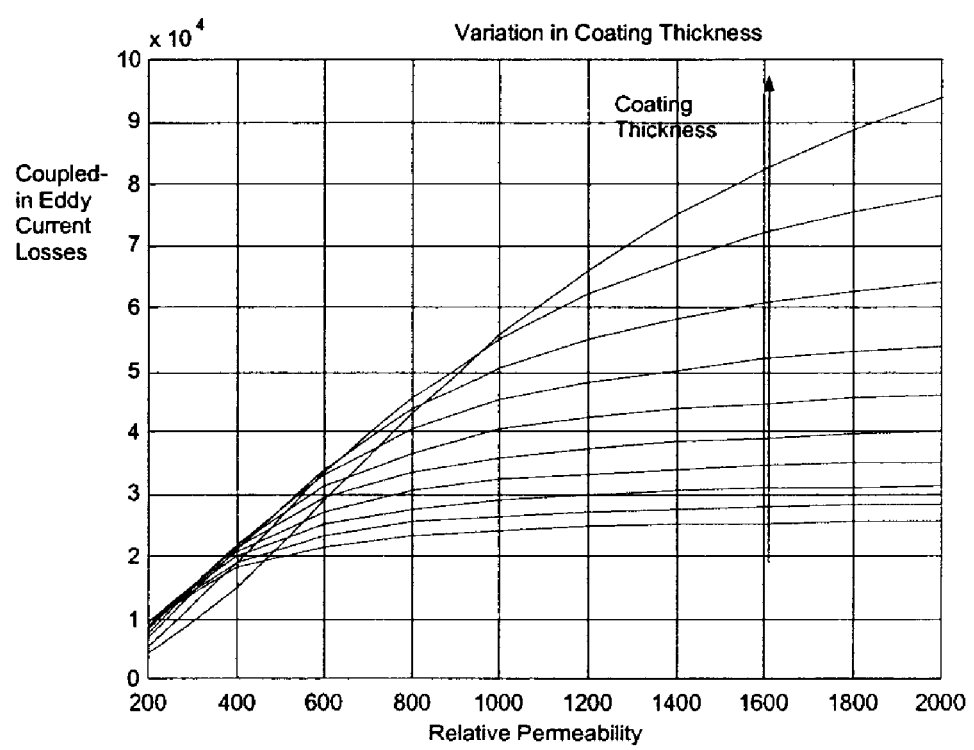
FIG. 13 illustrates a schematic view of Eddy Current vs. permeability with coating thickness as a parameter in accordance with the principles of the present invention.
Figure 14:
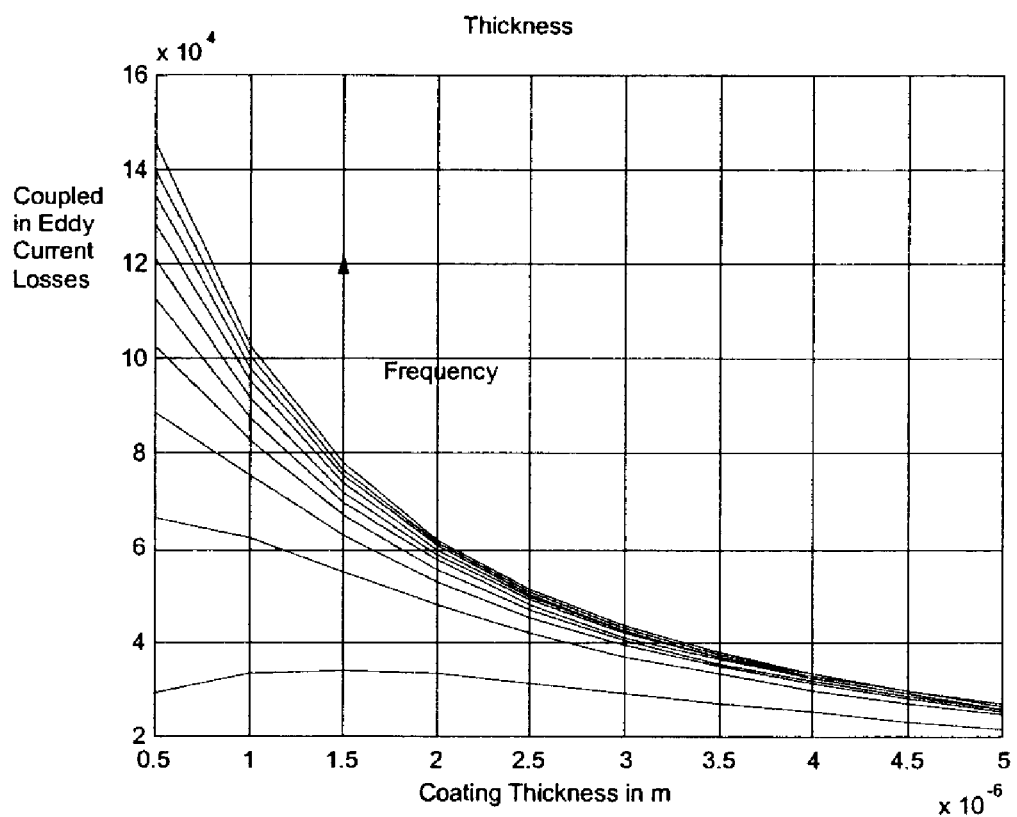
FIG. 14 illustrates a schematic view of Eddy Current vs. coating thickness with frequency as a parameter in accordance with the principles of the present invention.

FIG. 13 shows a picture similar to FIG. 12. It is a result of varying the ratio of the frequency affecting the coating thickness. A maximum value is also found when a typical coating thickness is used with a specific frequency. At higher frequencies, the coating thickness can be under 0.5 $\mu$m.

A very conductive thin coating around a core with high permeability improves the absorption of the heat generated. The heat energy is primarily produced in the coating. The thickness of the gold coating (a steel coating is conceivable) depends on the chosen excitation frequency and on the permeability of the core. At a relative permeability of several thousand, the gold coating is preferably less than 0.5 $\mu$m if the core only has a diameter of 90 $\mu$m. High excitation frequencies (>500 kHz) also require a very thin coating (<0.5 $\mu$m).

The Curie effect is indirectly contained in the permeability variation. Thus, permeability decreases at higher temperatures. The behaviour of the permeability temperature ratio is, therefore, material dependent. Depending on the magnitude of the permeability value in a normal state and after warming, the performance can drop by factors up to several 100,000.

The following table 1 lists the ferromagnetic materials that can be used as starting materials for the process described here.

TABLE 1

| Name of Material | Curie Temperature ° C. |
|---|---|
| Cobalt in pure form | 1130 |
|  | −168 |
| Dysprosium in pure form | 770 |
| Iron in pure form | 16 |
| Gadolinium in pure form | 385 |

To develop a SLS having a defined Curie temperature, an alloy is produced from a ferromagnetic and a non-ferromagnetic material, so that the Curie temperature, according to the ratio of components, falls below that of the pure ferromagnetic material.

The alloys can be nickel-copper alloys (Table 2), Nickel Palladium alloys (Table 3), Palladium Cobalt alloys (Table 4), Nickel-Iron Alloys; and Nickel-Silicon alloys (Table 5).

TABLE 2

Nickel-Copper alloys

| Material | Supplier | Curie temperature | Frequency Used | Biocompatibility |
|---|---|---|---|---|
| Ni 28% Cu | Ames Laboratory, Materials Preparation Center, Ames, IA, USA | 60 | 100 kHz | doubtful, coating necessary, invitro corrosion |
| Ni 29.6% Cu |  | 50 |  | doubtful, coating necessary, invitro corrosion |
| Ni 29.6% Cu |  | 50 | 90 kHz | doubtful, coating necessary, invitro corrosion |
| Ni 28% Cu | Ames Laboratory, Materials Preparation Centre, Ames, IA, USA | 60 | 100 kHz | Object of cited investigation: corrosion |

TABLE 3

Nickel Palladium alloys

| Material | Curie temperature in ° C. | Biocompatibility |
|---|---|---|
| Ni Pd in various ratios | 43–58 | no information |

TABLE 4

Palladium Cobalt alloys

| Material | Curie temperature in ° C. | Biocompatibility |
|---|---|---|
| Pd 6.15% Co | 50 | probably |

This alloy is interesting because besides having ferromagnetic properties, it also behaves like palladium in pure form. Looking at its material properties, it has an extraordinary corrosion resistance in a very broad pH spectrum. Palladium alloys have been used for quite some time in dental medicine for permanent oral implants, and besides palladium's biocompatibility, there is clinical evidence of mechanical durability. Additionally, there is extensive clinical experience since its introduction in 1986 regarding its use in branchy-therapy with radioactive $^{103}$Pd implants for treating prostate carcinoma. In conjunction with the above named Pd—Co alloy, it is possible to reach a Curie temperature of 50° C. in vitro and in calorimetric experiments.

Nickel-Iron Alloys

Biocompatibility is primarily achieved through the gold coating. In a study of simulated tissue by means of cellulose and a controlled flow of water, a stable Curie temperature of 50° C. is maintained at different water flow rates.

TABLE 5

Nickel-Silicon alloys

| Name of Material | Curie Temperature in ° C. | Biocompatibility |
|---|---|---|
| Ni 4% Si | 40–60° C. | cytotoxic, must be coated possible invitro corrosion |

There is data for in vitro as well as in vivo Ni Si Thermoseeds. The pure uncoated Ni Si alloys are very cytotoxic in vitro and in vivo, so that a coating, e.g. in the form of plastic catheters, is necessary. Furthermore, in production, so-called dendrite arms appear, which can be reduced at considerable cost; however, they do negatively impact the ferromagnetic properties. The process to reduce the dendrite arms leads to considerable irregularities in the surface, which with intravascular use, could lead to considerable thrombogenesis.

Further, materials for SLS are listed in Table 6.

TABLE 6

| Name of material | Curie temperature In ° C. | biocompatibility |
|---|---|---|
| Fe3O4 bone cement | 50–60° C. | no information |
| ferromagnetic glass ceramic | 43.5° C. | no information |

6. Temperature Considerations

In reaction to localized warming of the cells, heat shock proteins are created that lead to a tolerance towards further thermal exposure. Cells that have become thermo tolerant in this way require about 100 hours to return to thermo sensitivity. Even a warming period of 2–3 hours to 42° C. produces thermo tolerances in individual cells.

When using the thermal alteration with the help of intra-discal antennae within ligaments, there was thermo coagulation of the unmyelinated nociceptive fibers at temperatures >42° C. Thereafter, nerve regeneration is frequently observed.

At temperatures of 60° C. to 80° C., collagen contractions at the molecular level has been reported (Hydrogen bonds are broken supporting the triple helix structure of collagen molecules). It has been noted that at temperatures above 60° C., a medial-necrosis, a narrowing of the artery walls, occurs as well as alteration of the elastic fibers. The cells that are destroyed are damaged at such temperatures through direct heat transfer. At temperatures above 80° C., vascular complications arose in newborn lambs with high frequency balloon angioplasty.

In summary, it can be stated that a desirable target temperature of 43° C. to 60° C. may be required. However, it cannot be exactly described by which means the desired effect of treatment of vulnerable plaque issue is yet achieved.

From these statements, based primarily on experiments with angioplasty, the assumption is derived that inductive SLS warming at somewhat lower temperatures can work because the SLS is placed adjacent to or directly next to the target cells, and does not have to be internally subject to pressure, as is the case with angioplasty.

Early trials at high temperatures proved to be ineffective and damaged vessels and surrounding tissue at an undesirably high rate. Lower temperatures did, however, not have the desired effect.

It is noted that a SLS temperature of 46° C. for a period of 1 or 2 minutes corresponds in effectiveness to a SLS temperature of 43° C. for about 20 to 25 minutes.

The term hypothermia is defined as a temperature in the human body that is higher than 41.4° C., since the physiological limits of counter-regulation are exceeded at this point. For this reason, the targeted temperature lies above the stated 41.4° C.

When cadaver arteries are treated with lasers, perforation occurs at temperatures starting at 75° C. Therefore, the targeted temperature is below this value.

There is a connection between increase and decrease of cellular thermo tolerance as well as the induction and accumulation of heat shock proteins (HSP). HSP 70 is induced by heat and reduces neointimal hyperplasia. Temperatures below 43° C. appear to have no effect, whereas temperatures above 60° C. result in unacceptable side effects even with short exposures. Consequently, the targeted temperature range lies between 43° C. and 60° C.

In the heating antenna device 25 as shown in FIG. 7, the induction coil has preferably about one to five windings of a copper tube, placed in such a manner that the side facing the carrier system is the magnetic field line entry point representing its south pole, and the side facing the patient is its north pole where the magnetic field line exits. The diameter of the induction coil 25 is about 30 cm. This results in, at the induction coil, an inductivity value of 32 $\mu$F, an oscillation frequency of about 210 kHz, and a capacity of 17.5 nF. The electric current measures 15 A, and voltage is about 600 V.

Also, a temporary implantable and retractable SLS deployed within a vessel, such as a coronary vessel, has excellent metal-to-tissue contact surface. The SLS becomes an ideal medium for applying thermal energy to the tissue needed for treatment. It is appreciated that the above described methods and apparatuses can also be adapted to other inner hallow spaces, such as esophagus, larynx, ureter, urethra and the like, within the scope of the present invention.

It is appreciated that the above-described heating device can be a stand alone heating unit, or configured such that the heating device is incorporated into a vulnerable plaque detecting device, such as MRI, whereby the detecting device also provides electric power to the heating device.

It should be understood that the invention is not limited to the particular embodiments described. The invention is to cover all modifications, equivalents, and alternatives falling within the spirit and scope of the invention as defined by the appended claims.

BRIEF DESCRIPTION OF REFERENCE NUMBERS ILLUSTRATED IN FIGS. 4–7

1 any coronary vessel
2 localization of suspected vulnerable plaque
3 descending aorta
4 aorta arch
5 left subclavian artery
6 left common carotid artery
7 brachiocephalic trunc
8 ascending aorta
9 guiding wire or guiding tube
10 distal tip of guiding wire or guiding tube 9
11 lumen opening of guiding wire or guiding tube 9
12 left ventricle
13 localization wire
14 tip of localization wire 13
15 marker of localization wire, MR visible
16 marking tube
17 tip of marking tube 16
18 marker of marking tube, MR visible
19 proximal end of tubing-wire-system 9,13,16
20 starting-position/starting-distance of wire 13
21 end-position/end-distance of wire 13
22 given point on marking tube 16
23 SLS, stent-like structure
24 patient with placed endoluminal SLS
25 sending antenna, H-Coil
26 resonant circuit
27 power supply and amplifier
28 SLS, in a tone alike form
29 SLS, concave formed
30 SLS, convex formed
31 SLS with holding hooks 32
32 SLS holding hooks of 31
33 SLS outer diameter
34 SLS inner diameter
36 SLS unexpanded, starting position
37 SLS expanded, working position
38 SLS folded after working position to be removed, ending position
39 SLS tube wall

What is claimed is:

1. An apparatus for treating vulnerable plaque, comprising:
   an implanted stent-like structure adapted to be placed in a cardiovascular vessel adjacent a vulnerable plaque tissue, wherein said stent like structure does not provide a radial force to hold a blood vessel open; and
   a heating assembly for heating the implanted stent-like structure to conduct heat into the vulnerable plaque tissue.

2. The apparatus of claim 1, wherein the heating assembly is a non-invasive inductive heating assembly.

3. The apparatus of claim 2, wherein the heating assembly comprises:
   an electric power supply;
   an amplifier unit; and
   a resonant circuit with an induction coil, whereby the induction coil includes a winding and is positioned at a defined axial distance from the implanted structure placed in a living being.

4. The apparatus of claim 3, wherein the induction coil includes a plurality of windings and has a diameter of 30 cm.

5. The apparatus of claim 1, further comprising a detecting assembly for detecting the vulnerable plaque tissue.

6. The apparatus of claim 5, wherein the detecting assembly detects the vulnerable plaque tissue by Magnetic Resonance Imaging (MRI).

7. The apparatus of claim 5, wherein the detecting assembly detects the vulnerable plaque tissue by infrared spectroscopy.

8. The apparatus of claim 5, wherein the detecting assembly detects the vulnerable plaque tissue by thermography.

9. The apparatus of claim 5, wherein the detecting assembly detects the vulnerable plaque tissue by a blood test.

10. The apparatus of claim 5, wherein the detecting assembly detects the vulnerable plaque tissue by ultrasound.

11. The apparatus of claim 5, wherein the detecting assembly detects the vulnerable plaque tissue by X-ray.

12. The apparatus of claim 1, wherein the stent-like structure holds itself at an inner vessel wall.

13. The apparatus of claim 1, wherein the stent-like structure is made of a material that possesses a relative magnetic permeability of higher than 100.

14. The apparatus of claim 1, wherein the stent-like structure is made of a material that possesses a relative magnetic permeability of higher than 100,000.

15. The apparatus of claim 1, wherein the stent-like structure is made of a material having a Curie temperature that lies approximately in a temperature range where the vulnerable plaque tissue is stabilized.

16. The apparatus of claim 1, wherein the stent-like structure is made of a material having a Curie temperature that lies approximately in a temperature range whereby the vulnerable plaque tissue is inhibited from proliferation.

17. The apparatus of claim 1, wherein the stent-like structure is made of a material that comprises at least one of nickel, cobalt, dysprosium, iron and gadolinium.

18. The apparatus of claim 1, wherein the stent-like structure is made of a material that comprises at least one of nickel-copper, nickel-palladium, palladium-cobalt, nickel-silicon and $Fe_3O_4$.

19. The apparatus of claim 1, wherein the stent-like structure includes a coating of high electroconductivity.

20. The apparatus of claim 1, wherein the stent-like structure includes a coating of a metal.

21. The apparatus of claim 1, wherein the stent-like structure includes a poorer heat conducting coating on an inner wall and a better heat conducting coating on an outer wall.

22. The apparatus of claim 1, wherein the stent-like structure is made of a material having a Curie temperature of above 37° C.

23. The apparatus of claim 1, wherein the stent-like structure is made of a material having a Curie temperature in the range of about 42° C. to 45° C.

24. A method of treating vulnerable plaque, comprising:
implanting a stent-like structure adjacent to the vulnerable plaque tissue, wherein said stent like structure does not provide a radial force to hold a blood vessel open; and
heating the implanted stent-like structure to conduct heat into the vulnerable plaque tissue for a period of time.

25. The method of claim 24, wherein implanting the stent-like structure includes implanting the stent-like structure temporarily.

26. The method of claim 24, wherein implanting the stent-like structure includes implanting the stent-like structure permanently.

27. The method of claim 24, wherein heating the implanted stent-like structure includes inductively heating the stent-like structure noninvasively.

28. The method of claim 24, further comprising detecting the vulnerable plaque by Magnetic Resonance Imaging (MRI).

29. The method of claim 28, further comprising locating the vulnerable plaque tissue by the MRI.

30. The method of claim 29, wherein the locating includes using a first marking device to mark a distal end of the vulnerable plaque tissue and a second marking device to mark a proximal end of the vulnerable plaque tissue to define the extent of the vulnerable plaque tissue.

31. The method of claim 24, further comprising removing the stent-like structure after heating.

32. The method of claim 24, wherein the stent-like structure holds itself at an inner vessel wall.

33. The method of claim 24, wherein the stent-like structure is made of a material that possesses a relative magnetic permeability of higher than 100.

34. The method of claim 33, wherein the stent-like structure is made of a material that possesses a relative magnetic permeability of higher than 100,000.

35. The method of claim 24, wherein the stent-like structure is made of a material having a Curie temperature that lies in an order of magnitude within temperature limits whereby the vulnerable plaque tissue is stabilized.

36. The method of claim 24, wherein the stent-like structure is made of a material having a Curie temperature that lies in an order of magnitude within temperature limits whereby the vulnerable plaque tissue is inhibited from proliferation.

37. The method of claim 24, wherein the stent-like structure is made of a material that is an alloy of materials selected from nickel, cobalt, dysprosium, iron and gadolinium.

38. The method of claim 24, wherein the stent-like structure is made of a material that is an alloy of materials selected from nickel-copper, nickel-palladium, palladium-cobalt, nickel-silicon and $Fe_3O_4$.

39. The method of claim 24, wherein the stent-like structure includes a coating of high electroconductivity.

40. The method of claim 24, wherein the stent-like structure includes a coating of a metal.

41. The method of claim 24, wherein the stent-like structure includes a poorer heat conducting coating on an inner wall and a better heat conducting coating on an outer wall.

42. The method of claim 24, wherein the stent-like structure is made of a material having a Curie temperature of above 37° C.

43. The method of claim 24, wherein the stent-like structure is made of a material having a Curie temperature of between 42° C. and 45° C.

44. The method of claim 24, further comprising detecting the vulnerable plaque tissue by infrared spectroscopy.

45. The method of claim 24, further comprising detecting the vulnerable plaque tissue by thermography.

46. The method of claim 24, further comprising detecting the vulnerable plaque tissue by a blood test.

47. The method of claim 24, further comprising detecting the vulnerable plaque tissue by ultrasound.

48. The method of claim 24, further comprising detecting the vulnerable plaque tissue by X-ray.

* * * * *